United States Patent
Erb et al.

[11] Patent Number: 5,107,032
[45] Date of Patent: Apr. 21, 1992

[54] PROCESS FOR THE PREPARATION OF O-PHTHALALDEHYDES

[75] Inventors: Dudley K. Erb, Flemington; Janet E. Goldstein, North Brunswick, both of N.J.

[73] Assignee: Noramco, Inc., Athens, Ga.

[21] Appl. No.: 616,168

[22] Filed: Nov. 20, 1990

[51] Int. Cl.$^5$ ............................................. C07C 45/00
[52] U.S. Cl. .................................. 568/435; 568/426; 568/437
[58] Field of Search .................... 568/426, 437, 435

[56] References Cited

U.S. PATENT DOCUMENTS

| | | | |
|---|---|---|---|
| 2,948,756 | 8/1960 | Bengelsdorf | 568/437 |
| 3,089,908 | 5/1963 | Schult et al. | 568/437 |
| 4,125,561 | 11/1978 | Redecker et al. | 568/437 |
| 4,206,152 | 6/1980 | Gosteli | 568/435 |

FOREIGN PATENT DOCUMENTS

| | | | |
|---|---|---|---|
| 0166131 | 12/1981 | Japan | 568/437 |
| 2103208 | 2/1983 | United Kingdom | 568/437 |

Primary Examiner—Werren B. Lone
Attorney, Agent, or Firm—Steven P. Berman

[57] ABSTRACT

A process for the preparation of o-phthalaldehydes is disclosed comprising the steps of (1) halogenating an o-xylene and (2) hydrolysis of the resulting tetrahalogeno-o-xylene.

3 Claims, No Drawings

PROCESS FOR THE PREPARATION OF O-PHTHALALDEHYDES

BACKGROUND OF THE INVENTION

The present invention relates to a process for the Preparation of o-phthalaldehydes.

The o-phthalaldehydes which are the subject of this invention have the following formula:

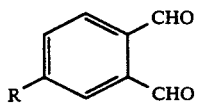

wherein R is selected from the group consisting of H, Cl, Br and $CO_2H$.

O-phthalaldehydes are well-known and long described in the literature. U.S. Pat. No. 4,206,152 describes a number of different processes for the preparation of these compounds. A process described in this patent comprises hydrolyzing at a pH of 4 to 11 an unsubstituted or substituted $\alpha,\alpha,\alpha',\alpha'$,-tetrahalogeno-o-xylene with an alkali metal salt, alkaline earth metal salt or ammonium salt of a lower carboxylic acid or of an aromatic carboxylic acid in the presence of an optionally substituted tetra lower alkyl ammonium as phase transfer catalyst and of an alkali metal carbonate or alkaline earth metal carbonate at a temperature above 60° C. When this process is carried out, it is found to take significantly longer periods of time than described in the patent to obtain the desired products and such is unsatisfactory from a commercial point of view.

SUMMARY OF THE INVENTION

It is an object of the present invention to provide an improved process for the preparation of o-phthalaldehydes.

It is another object of this invention to provide a process for the preparation of o-phthalaldehydes in good yields in relatively short periods of time.

Other objects of this invention will be set forth in or be apparent from, the following detailed description of the invention.

The foregoing objects and other features and advantages of the present invention are achieved by a process comprising the steps of (1) halogenating an o-xylene and (2) hydrolysis of the resulting tetrahalogeno-o-xylene.

DETAILED DESCRIPTION OF THE INVENTION

The foregoing objects are obtained in a process comprising the steps of:

(1) halogenating an o-xylene of the formula

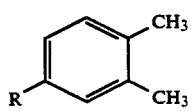

wherein R is selected from the group consisting of H, Cl, Br and $CO_2H$, to form an $\alpha,\alpha,\alpha',\alpha'$, -tetrahalogeno-o-xylene of the formula:

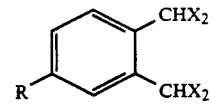

wherein X is Cl, Br or I; and (2) hydrolyzing the $\alpha,\alpha,\alpha',\alpha'$tetrahalogeno-o-xylene (II) by dissolving it in a short-chain alkyl acid, such as formic acid, acetic acid and propionic acid, and metering in a suitable alkali, such as sodium or potassium hydroxide, to obtain the desired o-phthalaldehyde of the formula

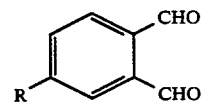

which may also be represented as:

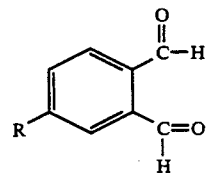

The $\alpha,\alpha,\alpha',\alpha'$,-tetrahalogeno-o-xylene is a known compound and the halogen substituent can be either Cl, Br or I; Preferably Cl or Br. The $\alpha,\alpha,\alpha',\alpha'$,-tetrachloro-o-xylene can be obtained by well-known procedures, e.g. by treatment of an o-xylene with elementary chlorine under irradiation with visible light (Houber-Wezl, Vol. 5/3, page 739). The $\alpha,\alpha,\alpha',\alpha'$-tetrabromo-o-xylene can also be obtained by well-known procedures, e.g., by treatment of an o-xylene with elementary bromine under irradiation with UV light (Organic Synthesis, Coll. Vol. IV, pg 807–808).

Various concentrations and amounts of acetic acid which is the preferred alkyl acid, have been utilized in performing this hydrolysis. The acetic acid ranged from glacial (anhydrous) to 20% water content. The amount of acetic acid ranged from 9.8 to 15.1 equivalents based on the halogenated precursor. Higher amounts of acetic acid can be utilized, but to no advantage. Smaller amounts of acetic acid resulted in very sluggish reactions. Significantly less acetic acid yields very impure product, if any at all.

The pH of these reactions must always remain on the acid side. A pH of 1.0 to 3.5 for the aqueous phase is the preferred range. It is known that under basic conditions, o-phthalaldehydes will undergo the Cannizarro reaction to form unwanted side products of the structure:

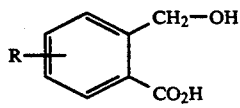

The concentration of sodium hydroxide, which is the preferred alkali, can range between 2 and 8 N. It is found that above 8 N, the product derived from these reactions showed some decomposition. Also, salts resulting from this reaction came out of solution when 6 and 8 N concentrations were employed, making the workup difficult. Reactions run below 2 N are not generally pursued because of the lack of productivity (throughput), but it is expected that they would work as well.

The temperatures ranged from about 96° to 146° C. and internal reactor pressures of 0 to 40 PSI. Equally good yield and quality of material was achieved within these temperature and pressure ranges. Temperatures significantly higher than 145° C. would result in some decomposition. The reaction times are preferably from 3 to 6 hours. It was found that extended reaction times generated product of significantly less pure composition.

All reactions should be carried out in glass or stainless steel autoclaves protected from light. It is a known fact that o-phthalaldehydes will photodecompose to yield the following compounds:

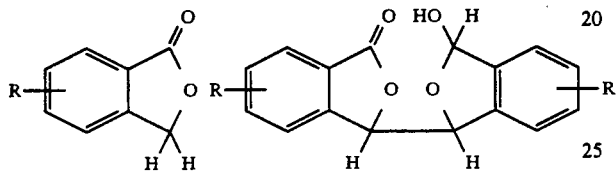

The product is isolated by extracting with toluene, followed by removal of the toluene under vacuum and distillation. The resulting solid product is recrystallized or flaked to obtain a flowing light yellow solid. Distillation of the product proved to yield very pure material. The product was easily distilled from impurities.

The o-phthalaldehydes obtained by the process of the present invention are utilized as reagents for the qualitative and quantitative determination of ammonia and primary amines. These compounds can also be utilized as disinfectant actives.

The following examples will illustrate in detail the manner in which the present invention may be practiced. It should be understood, however, that the invention is not confined to the specific limitations set forth in the individual examples, but rather to the scope of the appended claims.

EXAMPLE I

Into an appropriately sized round bottom flask equipped with a heating mantle, a gas inlet tube, overhead mechanical stirrer, thermometer and condenser was charged 1,872 grams o-xylene. The contents of the flask were purged with nitrogen, then warmed to 142° C. and chlorine was introduced into the vessel below the reaction mixture surface. The temperature of the reaction mixture reaches a maximum of 200° C. After a total of 6,942 grams chlorine were introduced, the reaction mixture was allowed to cool to room temperature spontaneously. The resulting crystals were collected by vacuum filtration.

The crude product (2,435 grams) were dissolved in 1,000 mL hot heptane. Upon cooling to room temperature, crystallization occurred. The crystals were isolated by vacuum filtration and washed twice with 500 mL ice cold heptane. This yielded 1,730 grams (40%) of slightly yellow $\alpha,\alpha,\alpha',\alpha'$-tetrachloro-o-xylene, MP 85°–89° C.

EXAMPLE II

Into an appropriately sized round bottom flask equipped with a heating mantle, a gas inlet tube, overhead mechanical stirrer, thermometer and condenser was charged 504 grams 4-chloro-o-xylene. The contents of the flask were purged with nitrogen, then warmed to 150° C. and chlorine was introduced into the vessel below the reaction mixture surface. The temperature of the reaction mixture reaches a maximum of 200° C. After a total of 1,574 grams chlorine were introduced, the reaction mixture was allowed to cool to room temperature spontaneously. The resulting crystals were collected by vacuum filtration and washed twice with 250 mL ice cold heptane.

The crude crystals (358 grams) were dissolved in 500 mL hot heptane. Upon cooling to room temperature, crystallization occurred. The mixture was cooled for an additional 1 hour at 0°–5° C. The crystals were isolated by vacuum filtration and washed with 250 mL ice cold heptane. A second crop of product was collected from the mother liquor to afford 265 grams (25%) 4,$\alpha,\alpha,\alpha'$,$\alpha'$-pentachloro-o-xylene, MP 63°–64° C. (95% pure by GC).

EXAMPLE III

Into a one liter 3-neck round bottom flask are charged 148 ml glacial acetic acid followed by 45.88 grams $\alpha,\alpha,\alpha',\alpha'$-tetrachloro-o-xylene prepared in Example I. The slurry is warmed. At 80° C. all solids are dissolved and a yellow solution results. The solution is warmed further to reflux. At 121° C., 480 ml 2 N sodium hydroxide are metered into the reaction mixture over 3.5 hours.

Stirring and heating are continued for an additional 4 hours. TLC of the reaction mixture shows only product. The reaction mixture is allowed to cool to approximately 60° C. The product is then extracted into 120 ml toluene. The product is then extracted an additional two times with 80 ml toluene.

The combined toluene extracts are then evaporated to a yellow oil on a rotary evaporator. The oil is placed under high vacuum (0.5 mm Hg) and crystals form. The product yield is 17.96 g(71%), MP 48°–52° C. and is identified by NMR and mixed melting point as o-phthalaldehyde.

EXAMPLE IV

Into a 500 ml 3-neck round bottom flask are charged 74 mL glacial acetic acid followed by 22.94 grams $\alpha,\alpha,\alpha',\alpha'$-tetrachloro-o-xylene prepared in Example 1. The slurry is warmed. At 80° C. all solids are dissolved and a yellow solution results. The solution is warmed further to reflux. At 121° C. 240 mL of 2 N sodium hydroxide are metered into the reaction mixture over 4.5 hours. Stirring and heating are continued for an additional 7 hours. TLC of the reaction mixture shows only product. The reaction mixture is allowed to cool to approximately 60° C. The product is then extracted into 60 mL toluene. The product is then extracted an additional 2 times with 40 mL toluene The combined toluene extracts are washed with 200 mL of 7% sodium bicarbonate solution and then 200 ml of water. The extract is stripped of solvent and the oil was allowed to crystallize, affording 10.1 gr (79%) o-phthalaldehyde. Identification is by TLC.

EXAMPLE V

Into a 2 liter 4-neck round bottom flask are charged 354 mL glacial acetic acid followed by 91.76 grams, $\alpha,\alpha,\alpha',\alpha'$-tetrachloro-o-xylene prepared in Example 1. The slurry is warmed. At 80° C. all solids are dissolved and a yellow solution results. The solution is warmed further to reflux. At 121° C. 827 mL of 2 N sodium hydroxide are metered into the reaction mixture over 4 hours. Stirring and heating are continued for an additional 4 hours. TLC of the reaction mixture shows only product. The reaction mixture is allowed to cool to approximately 60° C. The product is then extracted into 125 mL toluene. The product is then extracted an additional 4 times with 125 mL toluene.

The combined toluene extracts are then evaporated to a yellow oil on a rotary evaporator. Crystallization from the 60 grams of yellow solution remaining took place overnight. The product was filtered off. Dry yield is 23.4 g (53.2%) Identification is by TLC.

EXAMPLE VI

Into a liter 3-neck round bottom flask are charged 190 mL glacial acetic acid followed by 53.67 grams $\alpha,\alpha,\alpha',\alpha'$,-tetrachloro-o-xylene prepared in Example 1. The slurry is warmed. At 80° C. all solids are dissolved and a yellow solution results. The solution is warmed further to 96° C. At 96° C. 484 mL of 2 N sodium hydroxide are metered into the reaction mixture over 4.33 hours. Stirring and heating are continued for an additional 19.5 hours. TLC of the reaction mixture shows only product. The reaction mixture is allowed to cool to approximately 60° C. The product is then extracted into 125 mL toluene. The product is then extracted an additional 4 times with 125 mL toluene.

The combined toluene extracts are then evaporated to a yellow oil on a rotary evaporator. The reaction product was distilled at a head temperature of 113°–121° C., and a pressure of 7 mm. Yield 21.62 grams (74.22% theory). Identification is by TLC.

EXAMPLE VII

Into a one liter stainless steel autoclave are charged 199.5 grams glacial acetic acid, 15 mls water, 161 mls 6N NaOH and 53.67 grams $\alpha,\alpha,\alpha',\alpha'$,-tetrachloro-o-xylene prepared in Example 1. The reaction vessel is sealed and heated with stirring to 124° C. The internal pressure rises to 26 PSI.

Stirring and heating are continued for 4.5 hours. The product is extracted with 500 mls of toluene. The solvent is removed to leave a residue which is identified as o-phthalaldehyde by TLC.

EXAMPLE VIII

Into a one liter 4-neck round bottom flask are charged 199.5 grams glacial acetic acid, 15 mls of water and 53.67 grams $\alpha,\alpha,\alpha',\alpha'$,-tetrachloro-o-xylene prepared in Example 1. The reaction mixture was heated to reflux (111° C.) 242 mls of 4 N NaOH are metered in over a period of 1 hr and 10 minutes.

The reaction mixture is transferred to a 1 liter autoclave and heated to 140° C. The reaction mixture is held at 140° C. with stirring for 3 hours. The reaction mixture is cooled to 60° C. and the product extracted with 125 mls of toluene. The product is extracted an additional 4 times with 125 ml toluene.

The combined toluene extracts are then evaporated to a yellow oil on a rotary evaporator. The product was distilled at ≦10 mm pressure and a head temperature of 125° C. to yield 25.23 gr (87.3%) o-phthalaldehyde.

EXAMPLE IX

Into a 1 liter autoclave are charged 225 grams glacial acetic acid, 52.2 grams 4, $\alpha,\alpha,\alpha',\alpha'$-pentachloro-o-xylene and 412.5 mls of 2 N NaOH. The reaction vessel is sealed and heated with stirring to 125° C. Stirring and heating are maintained for 24 hours. The reaction mixture is cooled to 60° C. and the product is extracted with 100 mls of toluene. The aqueous layer is extracted 4 additional times with 100 mls of toluene at 60° C.

The combined toluene extracts are then evaporated to an oil on the rotary evaporator. The oil is distilled at a vacuum of 0.5 mm and a head temperature of 156°–158° C. to give 20.9 grams of product. This product is recrystallized from 11.5 mls of toluene to give 19 grams (60%) 4-chloro-o-phthalaldehyde with a melting point 79.5°–80.5° C. The product is identified by mass spectroscopy and NMR.

What is claimed is:

1. A process for the preparation of o-phthalaldehydes of the formula:

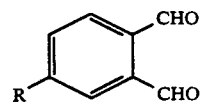

wherein R is selected from the group consisting of H, Cl, Br and Co$_2$H;

comprising the steps of a) halogenating an o-xylene of the formula

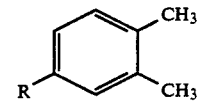

to form $\alpha,\alpha,\alpha',\alpha'$-tetrahalogeno-o-xylene of the formula

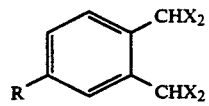

wherein X is selected from the group of Cl, Br and I; and b) hydrolyzing the $\alpha,\alpha,\alpha',\alpha'$-tetrahalogeno-o-xylene wherein the hydroylis is carried out in a short chain alkyl acid in the presence of alkali and wherein the temperature is from about 90° to 146° C. and the pressure is from about 0 to 40 PSI.

2. The process of claim 1 wherein X is Cl.

3. The process of claim 1 wherein X is Br.

* * * * *